United States Patent
Lacombe et al.

(10) Patent No.: US 8,080,383 B2
(45) Date of Patent: Dec. 20, 2011

(54) METHOD OF DISCRIMINATING AT LEAST TWO CELL POPULATIONS, AND APPLICATION

(75) Inventors: Francis Lacombe, Pessac (FR); Francis Belloc, Pessac (FR); Sylvie Veriac, Montpellier (FR); Didier Lefevre, Saint Clement de Riviere (FR)

(73) Assignee: Horiba Abx Sas, Parc Euromedicine, Motpellier Cedex 4 (FR)

( * ) Notice: Subject to any disclaimer, the term of this patent is extended or adjusted under 35 U.S.C. 154(b) by 492 days.

(21) Appl. No.: 12/158,597

(22) PCT Filed: Dec. 5, 2006

(86) PCT No.: PCT/FR2006/002645
§ 371 (c)(1),
(2), (4) Date: Jan. 23, 2009

(87) PCT Pub. No.: WO2007/080245
PCT Pub. Date: Jul. 19, 2007

(65) Prior Publication Data
US 2009/0311678 A1   Dec. 17, 2009

(30) Foreign Application Priority Data
Dec. 20, 2005  (FR) ..................................... 05 12948

(51) Int. Cl.
*G01N 33/567*  (2006.01)
*G01N 21/76*  (2006.01)

(52) U.S. Cl. ...... 435/7.21; 435/7.1; 435/7.23; 435/7.24; 435/287.2; 436/10; 436/56; 436/164; 436/172; 422/82.05; 422/82.08

(58) Field of Classification Search ............. 435/2, 7.21, 435/7.23, 7.24, 40.5, 285.2, 287.1, 287.2, 435/288.7, 7.1; 436/10, 17, 56, 63, 164, 436/165, 171, 174, 175, 177, 536, 546, 172; 422/82.01, 82.05, 82.06, 82.07, 90, 91, 82.08
See application file for complete search history.

(56) References Cited

U.S. PATENT DOCUMENTS
7,625,712 B2 * 12/2009 Paul et al. .................... 435/7.21

FOREIGN PATENT DOCUMENTS
EP  0 633 462 A2  1/2009
(Continued)

OTHER PUBLICATIONS
T. Hawley, et al., "Four-color flow cytometric detection of retrovirally expressed red, yellow, green, and cyan fluorescent proteins", Biotechniques, May 2001, p. 1028-1034, vol. 30, No. 5.
(Continued)

*Primary Examiner* — Gail R Gabel
(74) *Attorney, Agent, or Firm* — Browdy and Neimark, PLLC

(57) ABSTRACT

A subject of the invention is a method for discriminating between and counting at least two populations of biological elements carrying specific characteristics, optionally present in a sample. The invention allows the clear and unambiguous detection of at least three populations of biological elements by the use of only two detection means, which means that at least two populations of biological elements are detected by one and the same detection means. The invention can be carried out if three different probes are used, each recognizing and becoming fixed to one of the populations of biological elements to be detected, each of the probes being itself rendered detectable by a different marker, two of said markers having two emission spectra having at least one common part (overlapping emission spectra) and the third having an emission spectrum having essentially no part in common with the other two (non-overlapping spectrum).

24 Claims, 3 Drawing Sheets

FOREIGN PATENT DOCUMENTS

WO          03/016866 A2      1/1995

OTHER PUBLICATIONS

D. Maurer, et al., "A single laser flow cytometry method to evaluate the binding of three antibodies", Journal of Immunological Methods, 1990, p. 43-47, vol. 135, No. 1-2.

K. Pattanapanyasat, et al., "Flow cytometric two-color staining technique for simultaneous determination of human erythrocyte membrane antigen and intracellular malarial DNA", Cytometry, Jan. 1992, p. 182-187, vol. 13, No. 2, Wiley-Liss, Inc.

A. Beavis, et al., "Detection of cell-surface antigens using antibody-conjugated fluorospheres (ACF): Application for six-color immunofluorescence", Biotechniques, Sep. 1996, p. 498-503, vol. 21, No. 3.

M. Brown, et al., "Flow cytometry: Principles and clinical applications in hematology", Clinical Chemistry, May 22, 2000, p. 1221-1229, vol. 46, No. 8.

* cited by examiner

METHOD OF DISCRIMINATING AT LEAST TWO CELL POPULATIONS, AND APPLICATION

FIELD OF THE INVENTION

The present invention relates to a method for detecting, discriminating between and counting biological elements present in a liquid, using the principles of flow cytometry, which can be adapted to the devices routinely used in haematology.

BACKGROUND OF THE INVENTION

The automatic haematology analyzers (automatic haematology machines) currently on the market are providing more and more possibilities for analyses and classifications of the elements analyzed.

Fluorescence measurement, already widespread in flow cytometry, is mainly used for the classification of elements by immunophenotyping. In the routinely-used automatic haematology machines, it is above all dedicated to the detection of supra-vital dyes used as molecular probes for the quantification of nucleic acids or other cellular components.

The use of immunological probes in routine haematology has not yet become widespread although a few embryonic tests have already seen the light of day with different constructors.

For example, BAYER (Bayer Diagnostics, Tarrytown, N.Y., USA), with the BAYER-TECHNICON H*1 was the first to propose, in lymphocyte typing, the use of cocktails of antibodies for determining different types of lymphocytes. In this case, the measurement of the antigen expressions being carried out not by fluorescence but by the measurement of light absorbance generated by an avidine-peroxidase compound having a great affinity for biotin, itself coupled to an antibody. Said antibody is specific to the target antigens of the surface molecules specific to the cell types characterized (CD4, CD8, CD2, CD19).

The ABBOTT CD4000, from ABBOTT (Abbott Laboratories, Abbott Park, Ill., USA), proposes analysis using two fluorescence wavelengths for carrying out, inter alia, immunophenotypings. The patent WO 98/02727 of Abbott Laboratories describes an apparatus of this type, making it possible to carry out marking with an antibody on a total blood sample. ABBOTT describes in detail in the patent an apparatus intended to produce antibody-antigen reactions on a total blood sample.

SUMMARY OF THE INVENTION

A simple, rapid, effective and specific phenotyping method must be able to be used in very simple automatic machines, of automatic haematology machine type, making it possible to work with a limited number of detectors. Even if the technologies are substantially the same, the automatic machines routinely used in haematology have characteristics different from the flow cytometers, in particular in terms of the number of measurement parameters which are reduced to what is strictly necessary, particularly in routine measurements. Moreover, as cost is a very significant limiting factor, simplification of the devices and the analyses that they allow to be carried out can only improve overall savings.

Flow cytometry is a technology making it possible to simultaneously measure multiple parameters corresponding to different physical characteristics of a biological element such as for example a cell or a cellular organelle. The biological elements are entrained in a liquid flow and the device records the behaviour of each of them when they pass into the measurement chamber in front of a light source.

This technology is in fact a combination of three systems:
1) Fluid system: Laminar flow which allows the biological elements in suspension to pass one-by-one in front of the light in the measurement chamber.
2) Optical system: Laser beam or other light source and different filters which make it possible to select appropriate excitation as well as emission wavelengths.
3) Electronic system: PMT (photomultiplier tube) or photodiode, which captures the light emitted, allowing its conversion to an electric signal and then to a digital signal.

In summary, the light source makes it possible to generate a light which will pass through the lenses and illuminate the biological elements passing through a measurement chamber. On contact with the biological element, part of the light is diffused. This light passes through several lenses and other diaphragms and is focussed on a photodiode type sensor to generate the FSC (Forward Scatter) measurement. This measurement, within the chosen range of angles, gives an indication of the size of the biological element.

Another part of the light is deflected orthogonally and passes through another set of lenses, and a set of semi-reflective mirrors, in order to be measured at the level of a sensor to generate the SSC (Side Scatter) signal. This orthogonal light measurement gives an indication of the density of the biological element as well as its granularity (structure).

Finally, light intensity measurements can be carried out by means of as many photomultiplier tubes or photodiodes as there are wavelengths and optical signals to be analyzed.

The passage of the biological elements through a cytometer requires a prior stage during which the biological element is rendered detectable, and therefore marked, by a probe specific to a structure or a function of said biological element, said probe having itself been rendered detectable beforehand.

When the probe marker is a fluorescent molecule the latter can absorb a photon in a wavelength range which is specific to it (excitation spectrum). Thus excited, the fluorescent molecule will return to its fundamental state, and release a photon with lower energy. A fluorescent molecule therefore possesses an excitation wavelength spectrum which is specific to it and in which it will absorb energy in order to re-emit it in the form of fluorescence (emitted fluorescence), according to an emission spectrum which is also characteristic. The emitted fluorescence wavelength is always greater (lower frequency) than the excitation wavelength.

The diffusion (FSC, SSC) and fluorescence signals will be converted into electrical signals by suitable detectors, then analyzed by a computer system.

Thus in flow cytometry, a fluorescence wavelength band is commonly associated with each probe or cocktail of probes used. Each probe is therefore coupled to a fluorochrome (fluorescent marker), the signals of which are measured on a single fluorescence channel, whether said fluorochrome is grafted to one or more types of probe.

Cost reduction could be achieved by the routine use of immunophenotyping parameters with a restricted number of fluorescence measurement channels in addition to the standard physical parameters chosen from axial diffusion (Forward Scatter or FSC), orthogonal diffusion (Side Scatter or SSC), impedance measurement volume etc.

The possibility of summing the fluorescence responses would make it possible to express several different markings on the same measurement channel and thus to multiply a system's analysis capacities and therefore its price/performance ratio, without however increasing the complexity of the device by the addition of measurement channels.

The difficulty when several probes are conjugated with the same fluorochrome, is that the expression of the biological characteristics recognized respectively by the different probes, will directly influence the total quantity of fluorescence emitted.

Thus, for example, if a biological characteristic is strongly present (for example an antigen at the surface of a cell) the quantity of probes marked and fixed, will be proportional to the quantity of said biological characteristics. Consequently the quantity of fluorescence emitted by said probe, itself proportional to the quantity of biological characteristics having fixed said marked probe, will be higher.

In parallel, if another biological characteristic of the same sample is weakly represented, the quantity of fluorescence emitted by the corresponding probe, conjugated to the same fluorochrome, will be too low and can pass unnoticed, being masked by the fluorescence of the first probe.

Of course, the same difficulties are encountered during the use of other types of marking.

One of the purposes of the present invention is precisely to allow the clear and unambiguous detection of at least three probes by the use of only two detection means. This therefore means that at least two probes are detected by one and the same detection means. This can be achieved if three different probes are used, each recognizing and becoming fixed to one of the biological elements to be detected or to one of the characteristics of the biological element(s), each of the probes being itself rendered detectable by a different marker, two of said markers having two emission spectra having at least one part in common (overlapping emission spectra) and the third having an emission spectrum having essentially no part in common with the other two (non-overlapping spectrum). The two (or n) markers having an overlapping emission spectrum are measured by a first detection means, the marker having the non-overlapping emission spectrum being measured by a second detection means.

Thus, the present invention involves:

(1)—balancing the differences in antigen expression or cellular characteristic by the emission yield of n probes coupled to n markers measured in one and the same detection band;

(2)—creating a ratio between the signals originating from the second detection means on the one hand, and the signals originating from the first detection means on the other hand, in order to use it as an axis constituting a matrix;

(3)—combining in two dimensions the ratio originating from item (2) on the one hand, and the signals originating from the first detection means on the other hand, for the purpose of improving the graphic representation, and therefore improving the characterization and quantification of the biological elements of interest.

By "biological element" is meant according to the invention for example a eukaryotic or prokaryotic cell, a group of cells, a cell fragment.

By "biological characteristics", is meant a component specific to the biological element studied, for example, a biological component of the cell such as a cellular organelle, a protein, a lipid, a carbohydrate, or also a nucleic acid (RNA or DNA).

By "probe" according to the invention, is meant any means making it possible to specifically identify a biological or chemical characteristic present in or on the biological elements studied. Said means which can be used according to the invention are perfectly known in particular in the fields of cell biology, molecular biology, immunology and flow cytometry. There can be mentioned without being limitative, the antibodies, nucleic acids (DNA or of RNA), chemical compounds, particularly intercalating chemical compounds, those which react to the ionic environment ($H^+$, $Ca^{++}$, etc.), lectins, ligands or other cell viability dyes.

By "marker of the probe" is meant any compound which by its nature is directly detectable either visually, or using an appropriate device, or detectable after excitation. Such a compound, once coupled to the probe renders the latter detectable. Fluorescent molecules can be mentioned whether these are for example chemical compounds or biological molecules such as proteins. All these products are available on the market and supplied by most of the distributors of laboratory chemical products, such as for example Sigma, Aldrich, Fluka, Riedel de Haen, etc.

It should be noted that in the same experiment on discrimination between populations of biological elements using the method according to the invention, it is possible to use probes of different natures (conjugated antibodies and marked nucleic acids or cell viability for example) once their detection can be carried out according to the criteria defined according to the invention (at least two overlapping emission spectra and one non-overlapping spectrum).

By "detection means" is meant according to the invention any means of detecting, or even quantifying, the marker of the probe. Said detection means is of course characteristic of the method used for rendering the probe detectable. Said detection means is in all cases composed of all of the physical components capable of detecting the marker of a particular probe. For example, if it is a fluorescence-emitting marker, the detection means is the assembly comprising optical lenses for observing the sample, spatial filters (diaphragm, "pin hole", etc), spectroscopic (dichroic, interferential) filters especially arranged in order to allow only the part of the spectrum called the "detection band" specific to the marker or markers to be measured and to the optoelectronic sensor itself (photodiode, photomultiplier tube etc.) to pass towards the sensor. This sensor is then connected electronically to the electronic acquisition chain which carries out the processing of the analogue and/or digital signal and finally data processing via a computer.

It can also be for example a fluorescence detector if the probe is marked using a fluorescent marker or if the probe is itself fluorescent, or also a spectrophotometer if the probe is a marker which is absorbent in a specific part of the chromatic spectrum of the excitation light.

By "emission spectrum" is meant according to the invention the distribution of the fluorescence intensity as a function of the wavelength in a band characteristic of the marker or probe itself. Generally such a spectrum has an intensity peak corresponding to the emission maximum. The detection can be carried out in a range comprised between two wavelengths, generally framing a given intermediate wavelength corresponding to the maximum emitted fluorescence peak (maximum detection peak).

By "detection band" is meant a range of wavelengths chosen from the emission spectrum of the marker or markers considered (for example, if it is a fluorescence-emitting marker, the detection band is a band chosen preferably around the maximum fluorescence emission peak). This detection band is defined by the spectral filtering incorporated in the detection means, via at least one interferential or band pass filter optionally assembled behind one or more dichroic mirrors.

By "overlapping emission spectra" is meant that, in the same detection means, in the case of two different markers, their emission spectra have a common zone. For example if there are two fluorescence emitting markers, their emission spectra are called overlapping emission spectra when they have a common emission range comprised between two wavelengths common to their two emission spectra. Generally such spectra have distinct maximum emission peaks.

By "essentially non-overlapping emission spectrum", is meant that in the case of three different markers two of which have overlapping emission spectra, the third has an emission spectrum having no significant overlapping/overlapping zone with either of the spectra of the other two markers.

On reading the above, it is therefore understood that if three probes are used which recognize three different biological characteristics, marked with three markers each having a different emission spectrum, but two of which are overlapping and one non-overlapping, the method uses only two detection means to the extent that the markers with overlapping spectra have a common detection band.

This is what constitutes the great originality of the method which is the subject of the invention compared with the methods known in the prior art which, in order to detect three biological characteristics, use three probes having three independent emission spectra which are analyzed by three different detection means.

For the overlapping markers, the judicious choice of the markers as regards their detection will lead to the choice of two markers which can correspond, one more effectively than the other, in the same detection band.

According to a variant of the invention, the emission yield in the detection band can be chosen to be inversely proportional to the expression of the biological characteristics consider ed. The choice of the detection band is also determined as a function of this expression in order not to mask a weak positive expression (this is the first balancing phase of the invention).

Thus, for example, for a weakly expressed antigen a marker is chosen having a high emission yield in the chosen detection band and for a strongly expressed antigen a marker is chosen having a lower emission yield in the same detection band. This makes it possible to control the quantities of markers measured in order to balance the emissions in inverse proportion to the level of expression of the antigens or probes considered.

The method according to the invention makes it possible to discriminate between and count biological elements simply, rapidly and effectively. It also makes it possible to use simple devices, which has the consequence of reducing both manufacturing costs and costs of use and maintenance. Moreover the automated analysis is facilitated.

Thus a subject of the invention is a method for discriminating between at least two populations of biological elements carrying specific characteristics, optionally presented in a sample, comprising the simultaneous marking of said populations of biological elements by three different probes, which are detectable or rendered detectable by three different markers, two of said markers of which (overlapping markers or OMs) each have an emission spectrum, said emission spectra overlapping each other and the third (non-overlapping marker or nOM) has an emission spectrum not essentially overlapping the spectra of the other two markers (non-overlapping emission spectrum);

the measurement by any appropriate means, of the total quantity of non-overlapping marker (q nOM), in a detection band chosen from the emission spectrum of said non-overlapping marker;

the measurement by any appropriate means, of the total quantity of overlapping marker (qOM) in a detection band common to the emission spectra of said overlapping markers, the establishment for each biological element analyzed, of the ratio (R) of the total quantity of non-overlapping marker to the total quantity of overlapping marker [R=(qnOM)/(qOM)]

the establishment by any means of a diagram showing the ratio (R) as a function of the quantity of biological elements marked by the overlapping markers [R=f(qOM)] and/or the quantification by any appropriate means, generally a computer, of the biological elements identified in said diagram or diagrams and corresponding statistical data.

The method according to the invention is a method which allows the discrimination between and counting of biological elements corresponding positively or otherwise to a given criterion. The purpose of the method is not to quantify the number of probes fixed per biological element. The method makes it possible to detect without ambiguity, in a sample, particularly a biological sample, populations of biological elements having the sought characteristic or characteristics.

According to the last stage of the method according to the invention, the analysis of a bi-parametric matrix with y-axis R and abscissa qOM makes it possible to improve the graphic representation, and therefore to improve the characterization and the quantification of the biological elements of interest.

According to the invention, the sample can be a natural biological sample, particularly a liquid natural biological sample. It can also be a non-natural cellular suspension, such as for example a culture medium. As natural biological liquids, there can be mentioned without being limitative, blood, urine, dissociated tissue, spinal cord, cephalorachidian liquid, pleural liquid or synovial liquid, the product resulting from an apheresis process or as a synthetic cell suspension, a culture medium of cells or microorganisms.

According to the invention the biological elements contained in the sample can be eukaryotic or prokaryotic cells, or a mixture of the two, or fragments of said cells, organelles. The probes which can be used according to the method of the invention can be identical or different, antibodies, nucleic acids (DNA or RNA), or also any molecular probe such as for example dyes specifically recognizing nucleic acids, enzyme substrates or also markers specific to proteins, receptor ligands, molecules sensitive to the ionic environment (pH, $Ca^{++}$, probes etc.) or any other molecule specific to the biological characteristics targeted.

When the probes are antibodies, these can be monoclonal or polyclonal, natural or recombinant, human or animal antibodies.

The probes, if they are not naturally detectable, must, in order to be detectable, be conjugated to a marker which can be recognized by the detection means, in the detection band chosen.

According to the invention, the markers serving to render the probe detectable, can be detectable chemical compounds capable of being grafted to the probes, intercalating or non-intercalating markers of nucleic acids, or also markers specific to proteins or any other molecule specific to the biological characteristics targeted. These types of probes included reactive and conjugated probes, antibody conjugates, molecules probes, cyanine dyes, Daylight dyes, nucleic acid probes, cell function probes, and fluorescent and proteins. In this respect there can be mentioned fluorescent or also absorbent dyes such as: Alexa FLUOR® 350, ALEXA FLUOR® 488, ALEXA FLUOR® 532, ALEXA FLUOR® 633, ALEXA FLUOR® 647, ALEXA FLUOR® 660, ALEXA FLUOR® 680, allophycocyanine, aminomethylcoumarin acetic acid, Cy2®, Cy 5.1®, Cy 5®, Cy 5.5®, dichlorofluorescein (DCFH), dihydrorhodamine (DHR), "enhanced GFP" (EGFP), Fluo-3, FLUORX®, fluorescein, 5-maleimide fluorescein, fluorescein isothiocyanate (FITC), PerCP, r-Phycoerythrin (PE), R-Phycoerythrin-Cyanine 5 tandem or SPECTRALRED® or CYCHROME®, R-PHYCOERYTHRIN-CYANINE 5.5 (PE-CY 5.5C)), r-PHYCOERYTHRIN-CYANINE 7 (PE-CY 7®), R PHYCOERYTHRIN-TEXAS RED-x®, Red 613®, Rhodamine 110, Rhodamine 123, S65L, S65T, Tetramethylrhodamine isothiocyanate, Texas Red x TEXAS-RED-x®, TRURED®, indo 1, nano crystals (Quantum Dots), Fura 2, Fura 3, quin, DS Red as well as the markers specific in particular to the nucleic acids (whether in the form of DNA or of RNA), such as for example intercalating or other cell viability dyes such as ethidium bromide or also thiazole orange, thiazole blue and their derivatives, thioflavine S, thioflavine T, thioflavine TCN®, diethylquinolythocyanine iodide (DEQTC), TOTO-1®, TO-PRO-1®, or also YOYO-1®, HOECHST® 33258, HOECHST® 33342, HOECHST® 34580, diamidino phenylindole (DAPI), propidium iodide, pyronine Y, 7-Aminoactinomycine D (7AAD), acridine orange, auramine O, calceine, New Methylene Blue, olamin-O, Oxazine 750, Astra blue, SYTOX® Green, SYTO 11®, SYTO 12®, SYTO 13®, SYTO 16®, SYTO 18®, SYTO 80®, SYTO 81® etc.

In a particular embodiment of the invention, when cell characteristics, for example antigens, are recognized by probes rendered detectable by overlapping markers, it is possible to choose a first so-called generic cellular characteristic. i.e. present and characteristic of all the biological elements considered. The expression of this cell characteristic being normally high in the biological elements, the marker which is grafted to the probe recognizing it can be that which corresponds more weakly in the detection band common to the two overlapping markers (OM). Such a probe makes it possible to verify that good cell populations are indeed concerned.

The second cell characteristic recognized by a probe rendered detectable by the other overlapping marker, can be a cellular characteristic less expressed on a population only of the biological elements studied. The marker which is grafted to said probe must be a marker which corresponds more strongly in the detection band common to the two overlapping markers (OM).

A probe marked by a third marker which is non-overlapping with it (nOM) and which is detected in a second detection band different from the first, corresponds to the third cellular characteristic studied.

The method according to the invention can be implemented in any device allowing the detection of markers. In this respect there may be mentioned as an example the detection of fluorescence whether emitted by a dye conjugated to a molecular probe such as an antibody or directly by a supravital fluorescent dye such as an intercalating or non-intercalating dye, specific to the nucleic acids, or also the detection of light absorbance or diffusion in particular in a range of defined wavelengths of the spectrum, whether these measurements are made by extinction or diffusion of the range of wavelengths or by spectrometry of a band chosen from the ultraviolet to the infrared. This absorbance can be that generated either by a dye conjugated to a molecular probe such as an antibody or directly by a supravital dye such as an intercalating or non-intercalating dye, specific to nucleic acids.

A subject of the invention is also the use of the method described previously for discriminating between at least two cell populations carrying specific characteristics and optionally presented in a sample. A use of the method can be envisaged in medical diagnosis, such as for example in the field of chronic lymphoid leukaemia (CLL) and acute leukaemia (AL) using anti-CD45, anti-CD19 and anti-CD5 antibodies; in the field of the detection of residual disease (Minimum Residual Disease, MRD) and leucocyte differentiation using anti-CD45, anti-CD16 and anti-CD11b antibodies; in the field of hematopoietic progenitors using anti-CD45, anti-CD34, anti-CD33 antibodies and 7-AAD or DAPI or other viability marker; in the field of inflammation and cell activation using anti-CD45, anti-CD64 and anti-CD163 antibodies; in the field of the detection or monitoring of infection with the HIV virus using anti-CD45, anti-CD8 or anti-CD4 and anti-CD3 antibodies: in the field of the type b Acute Lymphoblastic Leukaemia (bALL) in children: in the field of observation of the spinal cord using anti-CD45, anti-CD19 and anti-CD10 antibodies or also the field of differentiation of the precursors of the B lymphocytes (haematogones) using anti-CD19, anti-CD10 and anti-CD38 antibodies. These descriptions are neither exhaustive nor limitative as these are merely the current state of medical knowledge.

Other characteristics of the invention will become apparent on reading the figures and examples which follow and which are given only by way of illustration without limitation of the invention.

BRIEF DESCRIPTION OF THE DRAWINGS

Thus.

Part 1A shows a standard graphic flow cytometry representation of the fluorescence of A+B (qOM) as a function of the fluorescence of C (qnOM).

Part 1B shows a graphic flow cytometry representation obtained according to the invention, of the ratio of the fluorescence of C (qnOM) to the total fluorescence of A+B (qOM) [qnOM/qOM] as a function of the total fluorescence of A+B (qOM) [qnOM/qOM=f(qOM)].

The implementation of the invention allows a distinction on the same fluorescence axis (the x-axis) between the biological elements expressing firstly (A+B+), secondly (A−B−) and thirdly (A+B−) or (A−B+).

Figure 2:
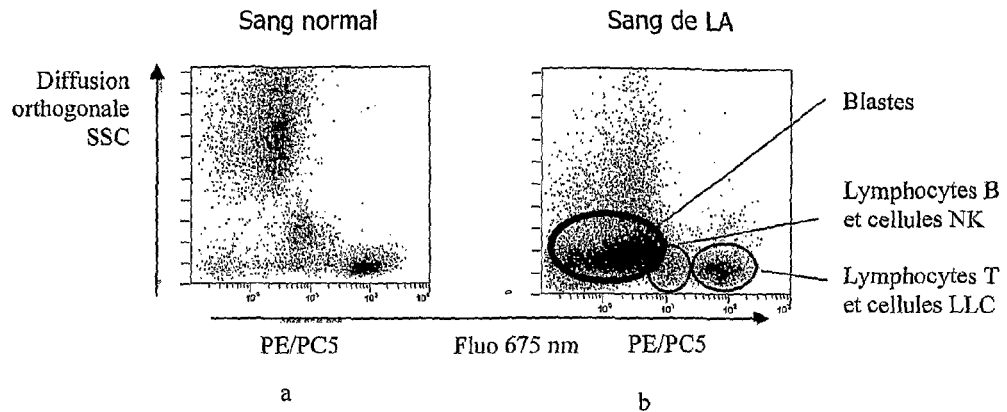

FIG. 2 shows the method according to the invention applied to the analysis of blood leucocytes in a normal blood sample (2a) and in a blood sample from a patient suffering from acute leukaemia (2b) after marking with an anti-CD45 antibody coupled to R-phycoerythrin (PE), an anti-CD5 antibody coupled to phycoerythrin-cyanine 5 (PC5) and an anti-CD19 antibody coupled to FITC. The expression of the CD45 alone makes it possible to identify the blasts present in this pathology.

Figure 1:
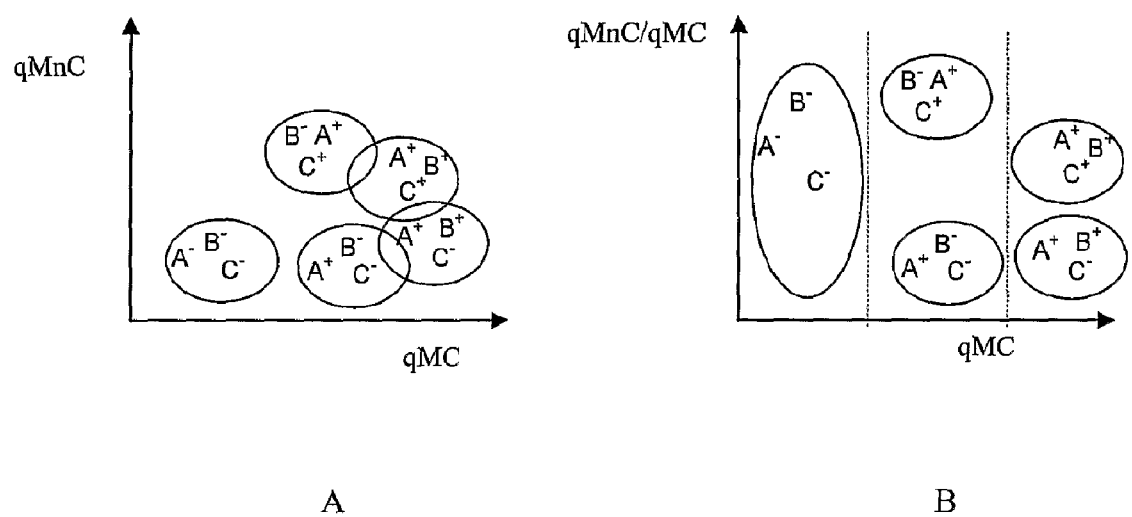
FIG. 1 is a diagrammatic representation of phenotypes of biological elements in which A and B are overlapping markers and C is a non-overlapping marker, which correspond respectively to probes (SA, SB and SC) rendered detectable, which recognize particular characteristics (PCA, PCB and PCC) of the bio logical elements considered.
Figure 3:
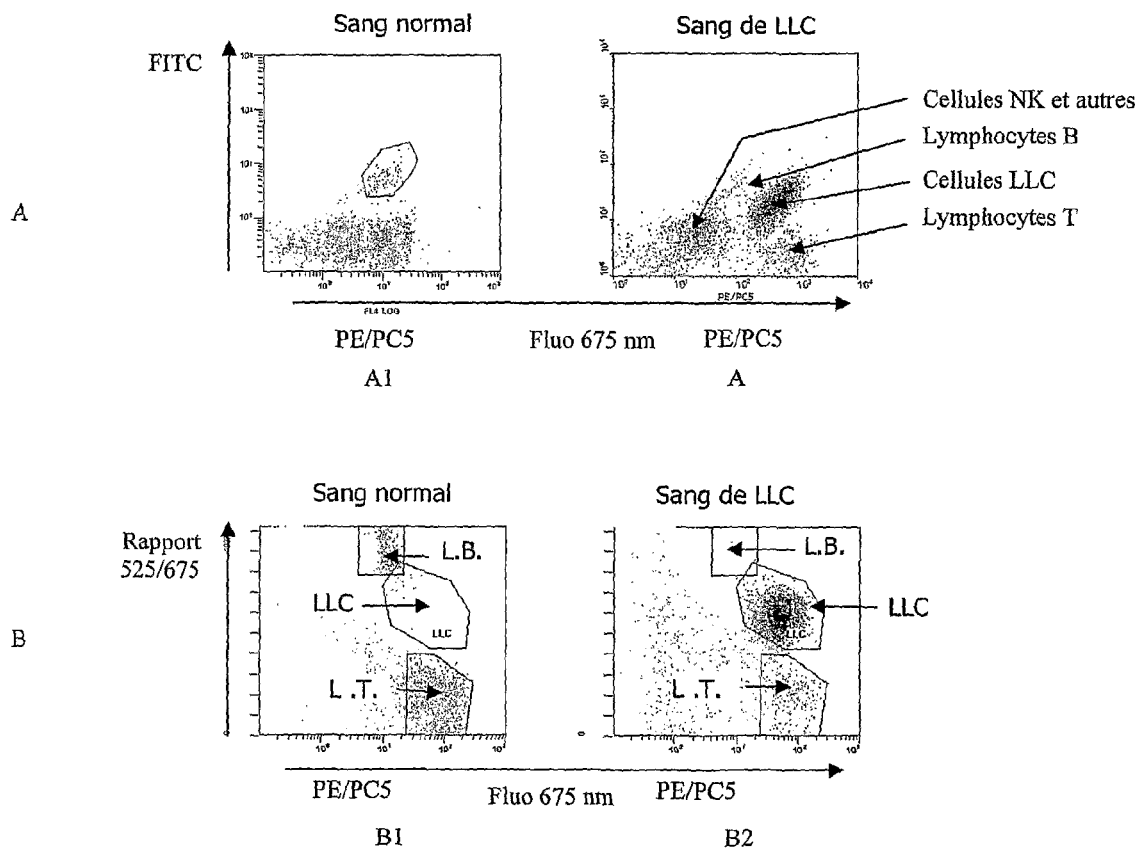

FIG. 3 represents samples of normal blood and of blood from a patient suffering from chronic lymphoid leukaemia (A2 and B2). FIGS. 3A1 and 3A2 show the results of the flow cytometry analysis, FIGS. 3B1 and 3B2 show the same results after application of the method according to the invention.

Figure 4:
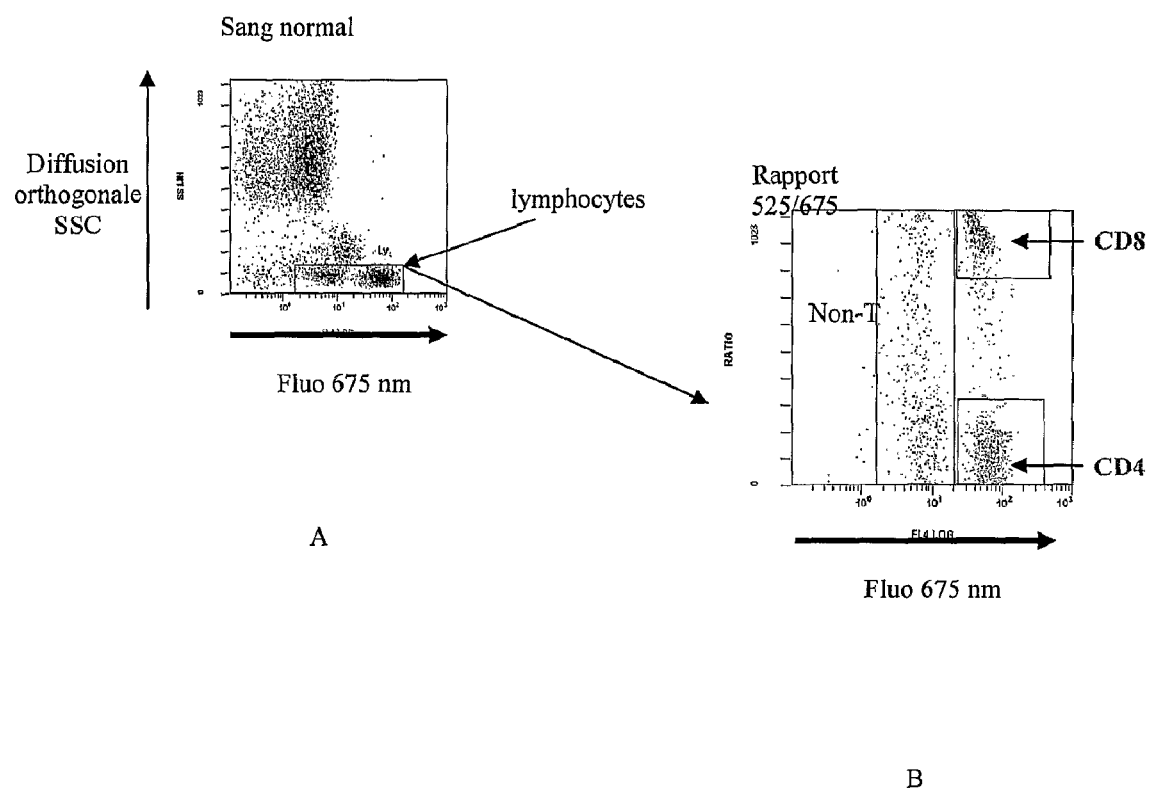

FIG. 4 shows the method according to the invention applied to the analysis of the blood T lymphocytes after marking with an anti-CD45 antibody coupled to the PE, an antibody anti-CD3 coupled to the PC5 and an anti-CD8 antibody coupled to the FITC. FIG. 3A shows the results of the flow cytometry analysis, FIG. 3B shows the same results after application of the method according to the invention.

DETAILED DESCRIPTION OF THE INVENTION

Example 1

The most frequent pathologies in onco-haematology are the different types of acute leukaemia (AL) and B lymphoid haemopathies, of which chronic lymphoid leukaemia (CLL) exhibits an incidence in constant progression ($30/10^6$).

Acute leukaemia (LA) can be characterized by a medullary invasion by proliferation of malignant haematopoietic cells.

Chronic lymphoid leukaemia (CLL) can be characterized by a proliferation of monoclonal lymphocyte cells, lymphoid cells of the atypical B line.

Leukaemic blasts of LA are characterized by a moderate expression of CD45 compared to that of the normal blood lymphocytes and monocytes.

Abnormal lymphocytes of the B-type CLL are characterized by the aberrant coexpression of the antigens CD5 and CD19 on the same cell whereas normal lymphocytes express either CD5 (T-line lymphocytes) or CD19 (B line lymphocytes).

The phenotypes of these cells can be summarized in the table below:

| Antigens | CD19 | CD45 | CD5 |
|---|---|---|---|
| Normal T lymphocytes | − | ++ | ++ |
| Normal B lymphocytes | + | ++ | − |
| LA blasts | | +/− | |
| CLL B lymphocytes | + | ++ | + |

Up to now, the analysis and identification of these different populations in a blood sample by flow cytometry have required the use of three different antibodies directed against the three antigens CD5, CD19 and CD45 and SSC orthogonal diffusion. For this analysis, each antibody is coupled to a different fluorochrome and each expression is measured at a different wavelength using different photomultipliers.

The use of the method according to the invention makes it possible to propose a system of marking and analysis by cytometry making it possible to detect and quantify, in the same sample of blood and during the same measurement, the possible presence of leukaemic cells using only two photomultipliers and SSC orthogonal diffusion.

On a flow cytometer, the optical filtering of the light signals is optimized for a given fluorochrome in order to measure its fluorescence in a wavelength band centred on its emission maximum: the fluorescein (FITC) is generally analyzed at 525 nm, R-phycoerythrin (PE) at 575 nm and R-phycoerythrin-cyanine 5 tandem (PC5) at 675 nm, for bandwidths of approximately 30 nm.

The emission spectra of PE and of PC5 are overlapping. They have for example in common the wavelength 675 nm at which PE has a much lower fluorescence yield than PC5. One of the original features of the method according to the invention resides in the measurement of the fluorescence of one of the fluorochromes (PE) at a wavelength different from that of its maximum emission, in this case the measurement of PE at 675 nm. Thus, at this wavelength, it becomes possible, by acting on different efficacies of the measurement system vis-à-vis two fluorochromes chosen for this purpose, to compensate for the significant differences in the expression of the antigens analyzed.

This principle is applied to the analysis of blood leucocytes after marking with an anti-CD45 antibody coupled to PE ($\lambda$max=575 nm), an anti-CD5 antibody coupled to the PC5 ($\lambda$max=675 nm n) and an anti-CD19 antibody coupled to the FITC ($\lambda$max=525 nm).

These markings are analyzed in a first detection band centred on 675 nm which is the maximum emission wavelength of PC5. The spectrum of the PE overlaps that of PC5. Analysis at 675 nm will therefore determine the total quantity of fluorescence emitted by PC5 and PE (qOM).

On the other hand, the quantity of fluorescence emitted by the anti-CD19 antibody coupled to FITC at 525 nm (qnOM) is analyzed.

The polynucleates and the monocytes are excluded from the windowing analysis on the basis of their light diffusion properties.

Protocol:

1) An aliquot of blood of a few microliters (5 to 50) is removed from a total peripheral blood sample and mixed with an aliquot of a few microliters (3 to 50) of the solution of the three conjugated antibodies described above.

2) The mixture is incubated at ambient temperature or regulated temperature, away from the light, for a period of a few minutes (1 to 30).

3) After the incubation period, an erythrocyte lysis reagent is added to the mixture, in order to obtain a final solution of blood at a desired specific concentration (1/40, 1/80, 1/100, etc.).

4) The lysed blood solution thus obtained is left to incubate for a few seconds dependent on the lysis reagent and incubation temperature (typically 15 to 30 seconds).

5) Then the solution is injected into a measuring assembly of the flow cytometer type in order to measure on each cell passing through an optical beam (most often a 488 nm laser for the dyes specified), the parameters of diffusion in the FSC axis, SSC orthogonal diffusion, green fluorescence at 525 nm (FL1) and red fluorescence at 675 nm (FL2). Stages 3 to 5 can be carried out automatically on a semi-automatic flow cytometry device or a specially designed automatic haematology machine and stages 1 to 5 can be automated on a specially designed automatic flow cytometry device.

Analysis of the fluorescence at 675 nm (FL1) as a function of the SSC orthogonal diffusion (see FIG. 2 A) makes it possible to discriminate between:

a very weakly fluorescent population corresponding to the LA blasts weakly expressing CD45, a population of an intermediate fluorescence corresponding to the lymphocytes expressing CD45 but not expressing CD5 (B lymphocytes and NK cells) and a very fluorescent population corresponding to the lymphocytes also expressing CD5 (T lymphocytes and CLL cells).

In this last population, analysis of the fluorescence at 525 mm makes it possible to identify the CLL cells also expressing CD19.

The application of the method according to the invention makes it possible to discriminate between the non-T lymphocytes, T lymphocytes and CLL cells by taking into account, for each cell, the ratio of the fluorescence at 525 nm to the fluorescence at 675 nm (qnOM/qOM). This ratio is expressed according to the truth table below:

| CD19 | CD45 | CD5 | Ratio CD19/CD45 + CD5 (qnOM/qOM) |
|------|------|-----|----------------------------------|
| −    | ++   | ++  | −                                |
| +    | ++   | −   | ++                               |
| +    | ++   | +   | +/−                              |

The distribution histogram obtained according to the invention [(qnOM)/(qOM)=f(qOM)] (see FIG. 2C) makes it possible to identify, separate and quantify three very distinctly separate populations.

- The normal T lymphocytes (T.L.) do not fluoresce at 525 nm but fluorescent significantly at 675 nm; they therefore have a very low ratio.
- The normal B lymphocytes (B.L.) fluoresce at 525 nm with an intermediate fluorescence at 675 nm, they therefore have a high ratio.
- The CLL cells express both CD5, CD45 and CD19, fluoresce at 525 nm and at 675 nm and their ratio is therefore intermediate (FIG. 2).
- The NK cells which express neither CD5 nor CD19 are excluded from the analysis on the basis of their fluorescence at 675 nm (CD45+, CD5− and CD19−).

Thus from one sample of blood, after marking by three fluorescent antibodies and lysis of the erythrocytes it is possible, in a single analysis, to discriminate between and count the T lymphocytes, B lymphocytes, and NK cells by measurement at two fluorescence wavelengths only.

The application of the method according to the invention makes it possible to discriminate between the T lymphocytes and CLL cells (FIG. 2B) which appear in the form of a single cloud in the diagram obtained according to a conventional analysis (FIG. 2A). The same applies in the case of the B lymphocytes and NK cells.

Moreover, the possible presence of acute leukaemia blasts or chronic lymphoid leukaemia cells can be detected and these cells can be counted.

The use of the method according to the invention can be applied to the diagnosis and monitoring of chronic B lymphoid pathologies, acute leukaemia, and to the monitoring of the residual disease during treatment.

Example 2

The method according to the invention can also be applied to the analysis of blood T lymphocytes after marking with an anti-CD45 coupled to the PE, an anti-CD3 coupled to the PC5 and an anti-CD8 coupled to the FITC. (FIG. 3).

1) An aliquot of blood of a few microliters (5 to 50) is removed from a total peripheral blood sample and mixed with an aliquot of a few microliters (3 to 50) of the solution of the three conjugated antibodies described above.

2) The mixture is incubated at ambient temperature or regulated temperature, away from the light, for a period of a few minutes (1 to 30).

3) After the incubation period, an erythrocyte lysis reagent is added to the mixture, in order to obtain a final solution of blood at a desired specific concentration (1/40, 1/80, 1/100, etc.).

4) The solution thus obtained is left to incubate for a few seconds dependent on the lysis reagent and incubation temperature (typically 15 to 30 seconds).

5) Then the solution is injected into a measuring assembly of the flow cytometer type in order to measure on each cell passing through an optical beam (most often a 488 nm laser for the dyes specified), the parameters of diffusion in the FSC axis, SSC orthogonal diffusion, green fluorescence at 525 nm (FL1) and red fluorescence at 675 nm (FL2).

Stages 3 to 5 can be carried out automatically on a semi-automatic flow cytometry device or a specially designed automatic haematology machine and stages 1 to 5 can be automated on a specially designed automatic flow cytometry device.

The markings with PE and PC5 are analyzed at 675 nm (qOM). The marking with FITC is analyzed at 525 nm (qnOM).

The polynucleates and monocytes are excluded from the analysis by their SSC orthogonal diffusion properties.

The diagram obtained according to the standard methods (FIG. 3A) of the fluorescence at 675 nm as a function of the SSC orthogonal diffusion makes it possible to detect a cloud representing the moderately fluorescent populations of lymphocytes expressing CD45 but not expressing CD3 (B lymphocytes and NK cells) and a very fluorescent population corresponding to the lymphocytes also expressing CD3 (T lymphocytes).

The application of the method according to the invention makes it possible to perfectly discriminate between the different populations (FIG. 3 B).

In particular this makes it possible to identify the CD8+ lymphocytes in the very fluorescent population corresponding to the lymphocytes also expressing CD3.

The CD4+ T lymphocytes do not fluoresce at 525 nm but fluoresce significantly at 675 mm and exhibit only a very low 525/675 ratio.

The CD8+ T lymphocytes fluoresce at 525 nm and at 675 nm, they therefore have a higher ratio.

The NK cells and the B cells which do not express CD3 are identified on the basis of their moderate fluorescence at 675 nm (Non-T).

The invention claimed is:

1. A method for discriminating between and counting at least two populations of biological elements having specific biological characteristics present in a sample, comprising simultaneously marking each said population of biological elements by three different probes which bind or react to predefined biological characteristics which are specific to the biological elements, the three different probes coupled to three different markers which render the biological characteristics detectable upon binding or reaction, wherein two of said markers are overlapping markers (OMs) each having an emission spectrum, said emission spectra overlapping each other and a third non-overlapping marker (nOM) having an emission spectrum not overlapping the spectra of the other two markers;

measuring the total quantity of non-overlapping marker (qnOM) in a detection band chosen in the emission spectrum of said non-overlapping marker;

measuring the total quantity of overlapping markers (qOM) in a detection band common to the emission spectra of said overlapping markers;

establishing a ratio (R) of the total quantity of non-overlapping marker to the total quantity of overlapping markers

[$R=(qnOM)/(qOM)$]; and establishing a diagram showing the ratio (R) as a function of the total quantity of biological elements marked by the overlapping marker [$R=f(qOM)$] wherein the diagram provides discrimination of the populations of biological elements which have predefined biological characteristics.

2. The method according to claim 1, wherein the sample is blood, urine, dissociated tissue, fluid in the spinal cord, cephalorachidian liquid, pleural liquid, synovial liquid, or a sample resulting from an apheresis process.

3. The method according to claim 1, wherein the biological elements optionally present in the liquid are eukaryotic cells or prokaryotic cells, or a mixture of the two, or fragments of said cells.

4. The method according to claim 1, wherein the probes, which are identical or different, are antibodies or nucleic acids (DNA or RNA) or dyes specific to the nucleic acids or enzymes or markers specific to proteins, receptor ligands or markers sensitive to the ionic environment or molecular characteristics of the biological element targeted selected from the group consisting of eukaryotic cells, prokaryotic cells, groups of cells and cell fragments.

5. The method according to claim 4, wherein the antibodies are monoclonal or polyclonal, natural or recombinant, human or animal antibodies.

6. The method according to claim 1, wherein the markers serving to render the probe detectable, are intercalating or non-intercalating markers of nucleic acids, or also markers specific to proteins or molecule characteristics of the biological element targeted selected from the group consisting of eukaryotic cells, prokaryotic cells, groups of cells, and cell fragments.

7. The method according to claim 6, wherein the markers are fluorescent or non-fluorescent markers.

8. The method according to claim 6, wherein the marker is chosen from the group consisting of antibody conjugates, molecular probes, cyanic dyes, fluorescent proteins, nanocrystals, nucleic acid probes, thiazole dyes, indole dyes, reactive probes and cell function probes.

9. A method for discriminating between and counting at least two populations of biological elements having specific biological characteristics present in a sample, comprising
simultaneously marking each said population of biological elements by three different probes which bind or react to predefined biological characteristics which are specific to the biological elements, the three different probes coupled to three different markers which render the biological characteristics detectable upon binding or reaction, wherein two of said markers are overlapping markers (OMs) each having an emission spectrum, said emission spectra overlapping each other and a third non-overlapping marker (nOM) having an emission spectrum not overlapping the spectra of the other two markers;
measuring the total quantity of non-overlapping marker (qnOM) in a detection band chosen in the emission spectrum of said non-overlapping marker;
measuring the total quantity of overlapping markers (qOM) in a detection band common to the emission spectra of said overlapping markers;
establishing a ratio (R) of the total quantity of non-overlapping marker to the total quantity of overlapping markers $$[R=(qnOM)/(qOM)];$$

establishing a diagram showing the ratio (R) as a function of the total quantity of biological elements marked by the overlapping marker [R=f(qOM)]; and
quantifying the populations of the biological elements having the predefined biological characteristics present in said diagram.

10. The method according to claim 9, wherein the sample is blood, urine, dissociated tissue, fluid in the spinal cord, cephalorachidian liquid, pleural liquid, synovial liquid, or a sample resulting from an apheresis process.

11. The method according to claim 9, wherein the biological elements optionally present in the liquid are eukaryotic cells or prokaryotic cells, or a mixture of the two, or fragments of said cells.

12. The method according to claim 9, wherein the probes, which are identical or different, are antibodies or nucleic acids (DNA or RNA) or dyes specific to the nucleic acids or enzymes or markers specific to proteins, receptor ligands or markers sensitive to the ionic environment or molecular characteristics of the biological element targeted selected from the group consisting of eukaryotic cells, prokaryotic cells, groups of cells and cell fragments.

13. The method according to claim 12, wherein the antibodies are monoclonal or polyclonal, natural or recombinant, human or animal antibodies.

14. The method according to claim 9, wherein the markers serving to render the probe detectable, are intercalating or non-intercalating markers of nucleic acids, or also markers specific to proteins or molecule characteristics of the biological element targeted selected from the group consisting of eukaryotic cells, prokaryotic cells, groups of cells, and cell fragments.

15. The method according to claim 14, wherein the markers are fluorescent or non-fluorescent markers.

16. The method according to claim 14, wherein the marker is chosen from the group consisting of antibody conjugates, molecular probes, cyanic dyes, fluorescent proteins, nanocrystals, nucleic acid probes, thiazole dyes, indole dyes, reactive probes and cell function probes.

17. A method for discriminating between and optionally counting at least two populations of biological elements having specific biological characteristics present in a sample, comprising
simultaneously marking each said population of biological elements by three different probes which bind or react to predefined biological characteristics which are specific to the biological elements, the three different probes coupled to three different markers which render the biological characteristics detectable upon binding or reaction, wherein two of said markers are overlapping markers (OMs) each having an emission spectrum, said emission spectra overlapping each other and a third non-overlapping marker (nOM) having an emission spectrum not overlapping the spectra of the other two markers;
measuring the total quantity of non-overlapping marker (qnOM) in a detection band chosen in the emission spectrum of said non-overlapping marker;
measuring the total quantity of overlapping markers (qOM) in a detection band common to the emission spectra of said overlapping markers;
establishing a ratio (R) of the total quantity of non-overlapping marker to the total quantity of overlapping markers [R=(qnOM)/(qOM)];
establishing a diagram showing the ratio (R) as a function of the total quantity of biological elements marked by the overlapping marker [R=f(qOM)] wherein the diagram provides discrimination of the populations of biological elements which have predefined biological characteristics; or
quantifying the populations of the biological elements having the predefined biological characteristics present in said diagram by comparing the ratio (R) as a function of the total quantity of biological elements marked by the overlapping marker [R=f(qOM)].

18. The method according to claim 17, wherein the sample is blood, urine, dissociated tissue, fluid in the spinal cord, cephalorachidian liquid, pleural liquid, synovial liquid, or a sample resulting from an apheresis process.

19. The method according to claim 17, wherein the biological elements optionally present in the liquid are eukaryotic cells or prokaryotic cells, or a mixture of the two, or fragments of said cells.

20. The method according to claim 17, wherein the probes, which are identical or different, are antibodies or nucleic acids (DNA or RNA) or dyes specific to the nucleic acids or enzymes or markers specific to proteins, receptor ligands or markers sensitive to the ionic environment or molecular characteristics of the biological element targeted selected from the group consisting of eukaryotic cells, prokaryotic cells, groups of cells and cell fragments.

21. The method according to claim 20, wherein the antibodies are monoclonal or polyclonal, natural or recombinant, human or animal antibodies.

22. The method according to claim 17, wherein the markers serving to render the probe detectable, are intercalating or non-intercalating markers of nucleic acids, or also markers specific to proteins or molecule characteristics of the biological element targeted selected from the group consisting of eukaryotic cells, prokaryotic cells, groups of cells, and cell fragments.

23. The method according to claim 22, wherein the markers are fluorescent or non-fluorescent markers.

24. The method according to claim 22, wherein the marker is chosen from the group consisting of antibody conjugates, molecular probes, cyanic dyes, fluorescent proteins, nanocrystals, nucleic acid probes, thiazole dyes, indole dyes, reactive probes and cell function probes.

* * * * *